(12) United States Patent
Gao et al.

(10) Patent No.: US 6,411,111 B1
(45) Date of Patent: Jun. 25, 2002

(54) ELECTRON-ELECTRO-OPTICAL DEBUG SYSTEM $E^2ODS$

(75) Inventors: Geng Ying Gao, Fremont; Kevin Weaver, San Jose, both of CA (US)

(73) Assignee: National Semiconductor Corporation, Santa Clara, CA (US)

( * ) Notice: Subject to any disclaimer, the term of this patent is extended or adjusted under 35 U.S.C. 154(b) by 0 days.

(21) Appl. No.: 09/571,085

(22) Filed: May 15, 2000

(51) Int. Cl.[7] .................... G01R 31/305; G01R 31/302; G01R 31/308; G01N 23/00
(52) U.S. Cl. .................... 324/751; 324/750; 324/753; 250/310
(58) Field of Search ................. 324/750, 751, 324/752, 500, 501, 71.3, 753; 250/310, 311

(56) References Cited

U.S. PATENT DOCUMENTS

| | | | | |
|---|---|---|---|---|
| 4,963,823 A | * | 10/1990 | Otto et al. | 324/751 |
| 5,150,043 A | * | 9/1992 | Flesner | 324/752 |
| 5,548,211 A | * | 8/1996 | Tujide et al. | 324/158.1 |

* cited by examiner

Primary Examiner—N. Le
Assistant Examiner—Anjan K. Deb

(74) Attorney, Agent, or Firm—Beyer Weaver & Thomas, LLP (57) ABSTRACT

A testing system comprising an electron beam probe, a photon beam probe, and a device under test (DUT) card holder which is positioned between the electron beam probe and the photon beam probe. A first valve is positioned between the electron beam probe and the DUT. A second valve, located on an opposite side of the DUT from the first valve, is positioned between the photon beam probe and the DUT. The first and second valve operate in cooperation to control the pressure surrounding the DUT card. One embodiment of the invention includes a first test chamber and a second test chamber. The first test chamber includes the area between the first side of the DUT card and the first valve. The second test chamber includes the area between the second side of the DUT card and the second valve. The present invention includes a method for using the test system of the present invention to test both the top and bottom surfaces of a semiconductor device. The method for using the test system manipulates the first valve and the second valve to selectively contain a vacuum pressure throughout the first test chamber and the area surrounding the DUT. The present invention includes a method for preparing an integrated circuit (IC) for testing by the testing system of the present invention. The present invention also includes a DUT card which secures and positions the DUT for testing within the testing system.

11 Claims, 7 Drawing Sheets

ELECTRON-ELECTRO-OPTICAL DEBUG SYSTEM E²ODS

FIELD OF THE INVENTION

The present invention relates generally to integrated circuit debugging systems, and more specifically to a system which combines the use of an electron beam probe and a photon beam probe.

BACKGROUND

Generally, the industry of semiconductor manufacturing involves highly complex techniques for integrating circuits into semiconductor materials. Due to the large scale of circuit integration and the decreasing size of semiconductor devices, the semiconductor manufacturing process is prone to processing defects. Testing procedures are therefore critical to maintain quality control. Since the testing procedures are an integral and significant part of the manufacturing process, the semiconductor industry constantly seeks more efficient testing procedures so that the entire manufacturing process may be improved.

Currently, electron beam scanning and photon beam scanning are two techniques that are sometimes used to test semiconductor devices. Electron beam scanning may be used to scan and test the metal trace layers of the semiconductor devices. Typically, electron beam scanning is performed from the front side of the devices. Photon beam scanning may be used to scan and test the diffusion areas embedded within the semiconductor material. Typically, photon beam scanning is performed from the backside of the devices. Both electron beam and photon beam scanning techniques are important for debugging the metal trace layers and the diffusion areas of integrated circuits in the semiconductor industry. Unfortunately, however, to perform both of these testing techniques, separate machines and facilities, and unique procedures for preparing for each test are necessary. The unique requirements for each technique present time and cost inefficiencies. Therefore, it would be desirable to develop a testing system, which uses both electron beam and photon beam scanning techniques, that is capable of testing semiconductor devices in an efficient and effective manner.

SUMMARY

The present invention presents an efficient and effective testing system which uses both electron beam and photon beam scanning techniques to scan and test semiconductor devices. The testing system of the present invention includes an electron beam probe, a photon beam probe, and a device under test (DUT) card holder which is positioned between the electron beam probe and the photon beam probe. The DUT card holder secures and positions a DUT card, which includes a device under test (DUT), during the operation of the test system. The electron beam probe and the photon beam probe each direct a beam of energy onto a first and second side of an IC device under test, respectively. A first valve is positioned between the electron beam probe and the DUT. A second valve, located on an opposite side of the DUT from the first valve, is positioned between the photon beam probe and the DUT. The first and second valve operate in cooperation to control the pressure surrounding the DUT card. One embodiment of the invention includes a first test chamber and a second test chamber. The first test chamber includes the area between the first side of the DUT card and the first valve. The second test chamber includes the area between the second side of the DUT card and the second valve. Time and cost savings are obtained by combining electron and photon beam probing capabilities into a single test system because the implementation of two separate probing systems is avoided.

Another aspect of the present invention is directed at a method for using the test system of the present invention to scan and test a first and a second surface of a semiconductor device. To facilitate electron beam probing, the DUT is isolated from the photon probe so that a vacuum pressure may be created within the first and second test chamber. After the vacuum pressure has been established, a first surface of the DUT is scanned with the electron beam. To facilitate photon probing, the DUT is isolated from the electron beam probe and exposed to the photon beam probe so that the second surface of the DUT may be scanned with the photon beam.

In another aspect, a method for preparing a packaged integrated circuit (IC) for testing by the testing system of the present invention is described. The preparation method involves preparing a first and a second surface of a packaged IC since the testing system will scan a first surface with an electron beam probe and a second surface with a photon beam probe. The preparation method includes removing packaging material from the first and second surfaces of a packaged IC as necessary, etching passivation material away from the first surface of the IC, and thinning the second surface of the IC.

In yet another aspect of the present invention, a DUT card which secures and positions the DUT for testing within the testing system is described. The DUT card includes a socket which is attached to a circuit card. The socket and circuit card both have openings which are aligned with each other. A DUT is secured by the socket opening such that both a first and a second surface of the DUT are accessible to beam probes through the socket and circuit card openings. In one embodiment of the present invention, the DUT card includes a locking mechanism capable of locking the DUT within the socket.

These and other features and advantages of the present invention will be presented in more detail in the following specification of the invention and the accompanying figures which illustrate by way of example the principles of the invention.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE INVENTION

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps have not been described in detail in order to not unnecessarily obscure the present invention.

Figure 1:
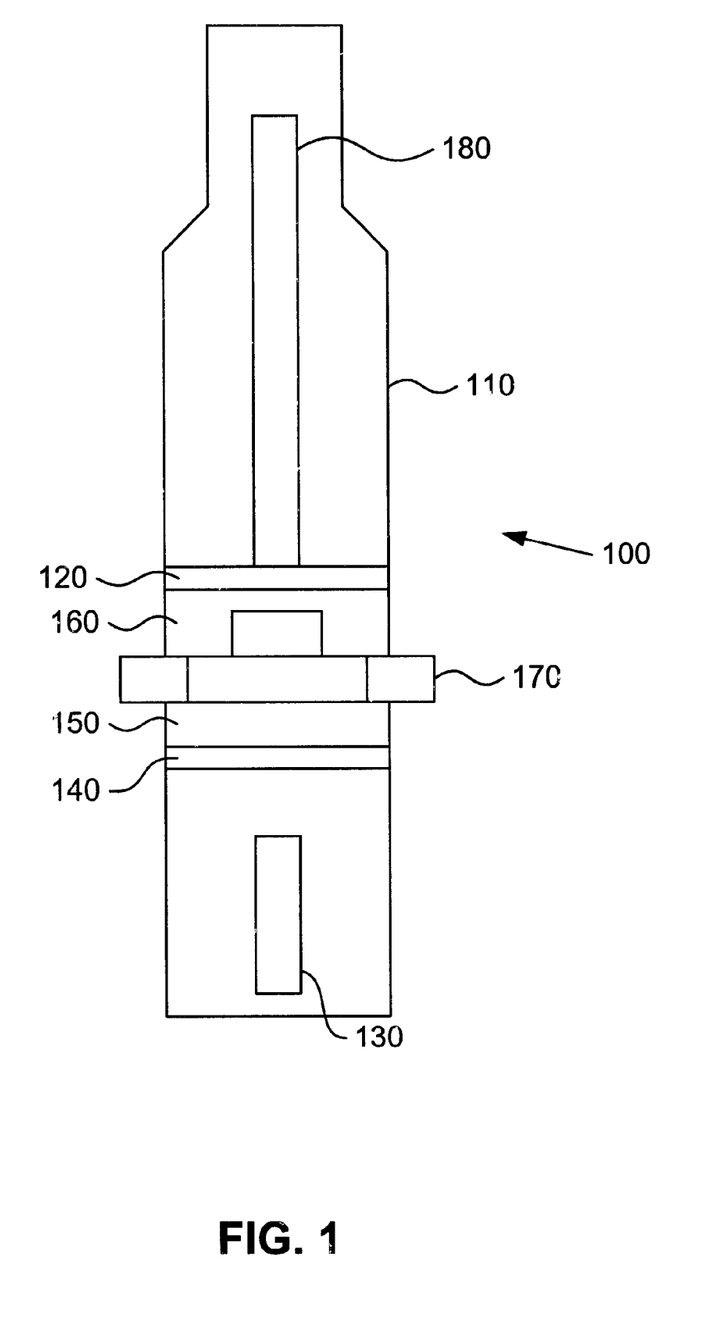
FIG. 1 illustrates one embodiment of an electron-electro-optical debug system (E²ODS).

FIG. 1 illustrates an electron-electro-optical debug system ($E^2ODS$) 100 in accordance with one embodiment of the present invention. The debug system 100 includes an electron beam probe 110, a photon beam probe 130 and a device under test (DUT) card holder 170 which is positioned between the electron beam probe 110 and the photon beam probe 130. The DUT card 170 secures and positions the device under test (DUT) during the operation of the debug system 100. The electron beam probe 110 includes an electron beam column 180 which has an opening positioned over the top surface of the DUT card 170. The electron beam column 180 provides a path along which an electron beam may travel. A first valve 120 is located at the opening of the electron beam column 180 so that the the pressure within the electron beam column may be controlled. A first test chamber 160 includes the area between the first valve 120 and the DUT card 170. A second valve 140 is located between the photon beam probe 130 and the DUT card 170. A second test chamber 150 includes the area between the second valve 140 and the DUT card 170. The second valve 140 and the first valve 120 operate in cooperation to control the pressure within the first test chamber 160, the second test chamber 150 and the electron beam column 180. Time and cost savings are obtained by combining electron and photon beam probing capabilities into a single test system because the implementation of two separate probing systems is avoided.

The electron beam probe 110 is used to probe the top surface of the device under test. More commonly, the top surface of the device under test is referred to as the "front side." The electron beam probe 110 may be of the type that is generally used in scanning electron microscopes (SEM). By way of example, a conventional SEM image may be produced by raster scanning a focused beam of electrons over a specimen. The electron beam is produced by using a magnetic condenser lens and an objective lens to focus electrons emitted from an electron emitter into an electron beam. The electron beam is directed at the device under test where the electrons then collide with and scatter off the surface of the device under test. An electron detector collects the scattered electrons which are then used to form an image of the surface of the device under test. A phenomenon called the "voltage contrast phenomenon" produces an intensity variation in the SEM image that is a function of the surface electrical potential. SEM images are useful diagnostic tools which may detect faults in the exposed surfaces of chips, such as a broken interconnect line.

To operate properly, the electron beam must be enclosed within a vacuum pressure zone so that the electrons are not obstructed by air particles while traveling to and from the surface of the device under test. The electron beam column 180, the first test chamber 160, the second test chamber 150, along with the first valve 120 and the second valve 140 operate to maintain a vacuum pressure along the paths which the electrons travel. The electron beam column 180 contains the electron emitter, the lenses used to focus the electron beam, the electron detector, and other various components of the electron beam probe 110. During the electron beam scanning process, the first valve 120 is opened and the second valve 140 is closed. The first valve 120 is opened to create an unobstructed pathway for the electrons to travel from the electron emitter, through the electron beam column 180, to the device under test. The second valve 140 is closed so that a vacuum pressure zone may be created within the electron beam column 180, the first test chamber 160 and the second test chamber 150. As a result, the DUT card 170 will be enclosed within a vacuum. A vacuum in both the first test chamber 160 and the second test chamber 150 is desirable since the DUT secured within the DUT card 170 would not be capable of providing an air-tight barrier between the test chambers.

Before and after the electron beam scanning process, the first valve 120 is closed in order to preserve a vacuum in the electron beam column 180. By preserving the vacuum within the electron beam column 180, less time is required to pump down the electron beam column 180 between separate electron beam scanning processes. This function of the first valve 120 may save substantial amounts of testing time since a relatively long amount of time, in comparison to the beam probing procedures, is required to create a vacuum within an enclosure.

The photon probe 130 is used to probe the bottom surface of the device under test. More commonly, the bottom surface of the device under test is referred to as the "backside." The photon beam probe 130, as generally known in the art, is a device which produces a high-energy beam of photons. In order to probe the device under test with the photon beam probe 130, the second valve 140 must be in the opened position so that an objective lens of the photon beam probe may be moved into an position adjacent to the device under test. As the second valve 140 is opened, the vacuum pressure zone created within the first test chamber 160 and the second test chamber 150 for the purpose of electron beam probing will be released. To maintain the vacuum within the electron beam column 180, the first valve 120 may be closed. As is generally known, vacuum pressure is not required for photon beam probing. In this particular embodiment, the first valve 120 and the second valve 140 are gate valves, however, these valves may be of any type capable of containing a vacuum.

The DUT card holder 170 is a device which holds and positions the device under test during the probing operations. Seals may be placed on the top and bottom surfaces of the DUT card 170 at the points where it is connected to the first test chamber 160 and the second test chamber 150. The seals help maintain the vacuum contained in the first test chamber 160 and the second test chamber 150. In one implementation of the invention, the device under test is a packaged integrated circuit. The packaged integrated circuit, sometimes called "a part," is a die which has been packaged within a protective plastic molding material and which has electrical contacts connected to the die. The electrical contacts allow the die to be electrically connected to a printed circuit board. In other implementations of the invention, the device under test may be a die which has not been packaged.

Figure 2:
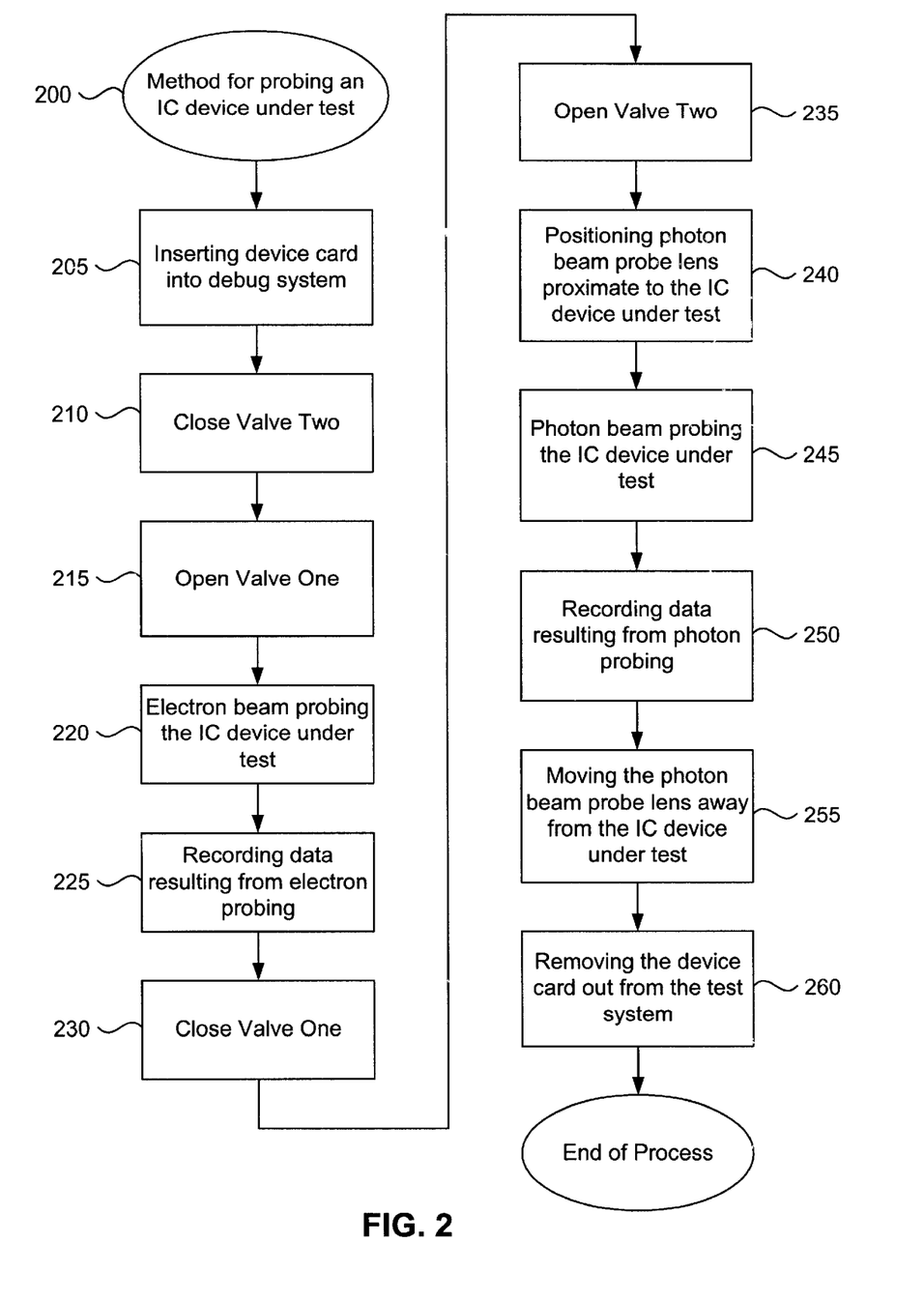
FIG. 2 is a flow diagram describing one implementation of the method for probing an IC device under test.

FIG. 2 is a flow diagram describing one embodiment of the method for probing an IC device under test 200. The method for probing 200 begins in block 205 by inserting the DUT card 170 into a slot positioned between the first valve 120 and the second valve 140. The DUT card 170 secures the device under test in a position such that when the DUT card is inserted into the debug system 100, the device under test is properly positioned to be probed by both the electron beam and the photon beam. The inserted DUT card 170 defines the separation between the first test chamber 160 and the second test chamber 150. In an alternative embodiment, the DUT card 170 may be added to the debug system 100 by clamping the first test chamber 160 and the second test chamber 150 to the top and bottom surfaces of the DUT card 170, respectively. Then, the electron beam probe 110 and the photon beam probe 130 may be clamped to the first test chamber 160 and the second test chamber 150, respectively.

In the described implementation, the debug system 100 will probe the device under test with the electron beam probe 110 first, and with the photon beam probe 130 second. The following description of sequences for probing and valve manipulations correspond to this particular probing order. It may be appreciated, that by altering the sequence of probing and valve manipulations, the order of the probing may be reversed.

Operation of the electron beam probe 110 requires a vacuum pressure environment so that the electron beam can move without interference from air particles. In order to create a vacuum environment along the path of the electron beam and surrounding the DUT card 170, valve two 140 is closed and valve one 120 is opened. These actions, represented in blocks 210 and 215, respectively, create an enclosed space extending throughout the electron beam column 180, the first test chamber 160 and the second test chamber 150. The opening of valve one 120 creates an unobstructed path for the electron beam to travel from the electron emitter, through the focusing lenses, to the device under test. This enclosed space is then pumped down to vacuum pressure, which may be, for example, in the range of approximately $1.0*10^{-9}$ to $1.0*10^{-5}$ torr. Of course, the actual vacuum pressure utilized for testing may be widely varied based on a variety of factors including the needs of a particular electron beam probe system being used and the nature of the testing being done.

Block 220 represents the use of the electron beam probe 110, in the vacuum environment, for directing an electron beam upon the device under test in order to scan the front side of the device under test. The scanning can be done in any appropriate manner based on the type of electron beam probe 110 being used. By way of example, scanning of the device under test may be performed in a manner similar to when specimens are viewed using a Scanning Electron Microscope (SEM). As with SEM microscopy, an electron beam is directed at the device under test so that electrons scatter off of the surface of the device under test. These scattered electrons are then collected and used to create an image of the surface of the device under test.

In block 225 the data and images resulting from the electron beam probing are recorded. This operation completes the electron beam probing process. Before proceeding onto the photon probing process, valve one 120 is moved into a closed position to seal the opening of the electron beam column 180. By closing valve one 120, a vacuum pressure may be preserved within the electron beam column 180. As will be described shortly, valve two 140 will be opened to allow for photon beam probing, which would result in allowing the vacuum pressure in the first test chamber 160 and the second test chamber 150 to be released. Maintaining a vacuum pressure in the electron beam column 180 avoids the need to recreate the full vacuum pressure before each electron beam probing process. This results in substantial time and cost savings.

It should be appreciated that it is generally desirable to make an effort to minimize the region around the device card holder that is subjected to a vacuum during the electron beam probing since the vacuum is released for the purpose of photon beam probing. This reduces the amount of vacuum that must be recreated before each electron beam probing process. In other words, the size of the first test chamber 160 and the second test chamber 150 should be minimized. One way to help reduce the volume of the region around the device card holder is to place the valves as close as practical to the device card holder.

In block 235, valve two 140 is opened so that the objective lens of the photon probe beam 130 may be positioned adjacent to the device under test. As valve two 140 is opened, the vacuum pressure which existed in the first test chamber 160 and the second test chamber 150 is released. The loss of the vacuum pressure surrounding the device under test is permissible since it is not required for photon beam probing. The operation of valve one 120 and valve two 140, together, control the pressure throughout the debug system 100 so that electron and photon beam probing may performed sequentially during a single testing procedure. Since the present invention allows a single debug system to perform both electron and photon beam probing, separate electron and photon beam probing machines and set-up procedures are avoided. The debug system 100 of the present invention therefore provides time and cost savings during the testing phase of semiconductor manufacturing.

In block 240, the objective lens of the photon beam probe 130 is moved adjacent to the backside of the device under test. The appropriate standoff distance between the photon beam probe 130 and the device under test will vary based on a number of factors including the type of probe being used, the region of the device under test that is to be examined, etc. Typically, the objective lens of the photon beam probe 130 is placed within approximately 1 millimeter of the backside of the device under test.

After the objective lens of the photon beam probe 130 is positioned adjacent to the device under test, photon beam probing may be performed as represented in block 245. Photon beam probing may be performed according to the techniques that are known by those of ordinary skill in the art. Photon probing utilizes a photon beam which has photon energies greater than the indirect band gap of the semiconductor being probed. For example, a photon beam having an energy greater than 1.1 eV and a wavelength of 1.06 um would allow the photon beam to penetrate to the diffusion areas in a silicon semiconductor device. When the photon beam is focused on the diffusion areas, the photons with energies greater than the band-gap are absorbed and the photons with energies less than the band-gap are transmitted. This is referred to as the electro-optical absorption effect. The reflected photons are then sampled and calculated to form waveforms based on the electro-optical sampling principle. The material composition of the semiconductor may be determined by measuring the photocurrent. For example, the quality of the doped areas in the semiconductor material may be measured. Data collection from the photon probing is collected and recorded in block 250.

In order to remove the device under test from the debug system 100, the photon beam probe lens must first be moved away from the DUT card 170. This is shown in block 255. Then, as represented in block 260, the DUT card 170 may be removed. At this point, the testing process is completed and the method of probing 200 may be restarted at block 205. It should be appreciated that the valve one 120 preferably remains closed while the DUT card 170 is removed in order to maintain the vacuum in the electron beam column 180.

Figure 3:
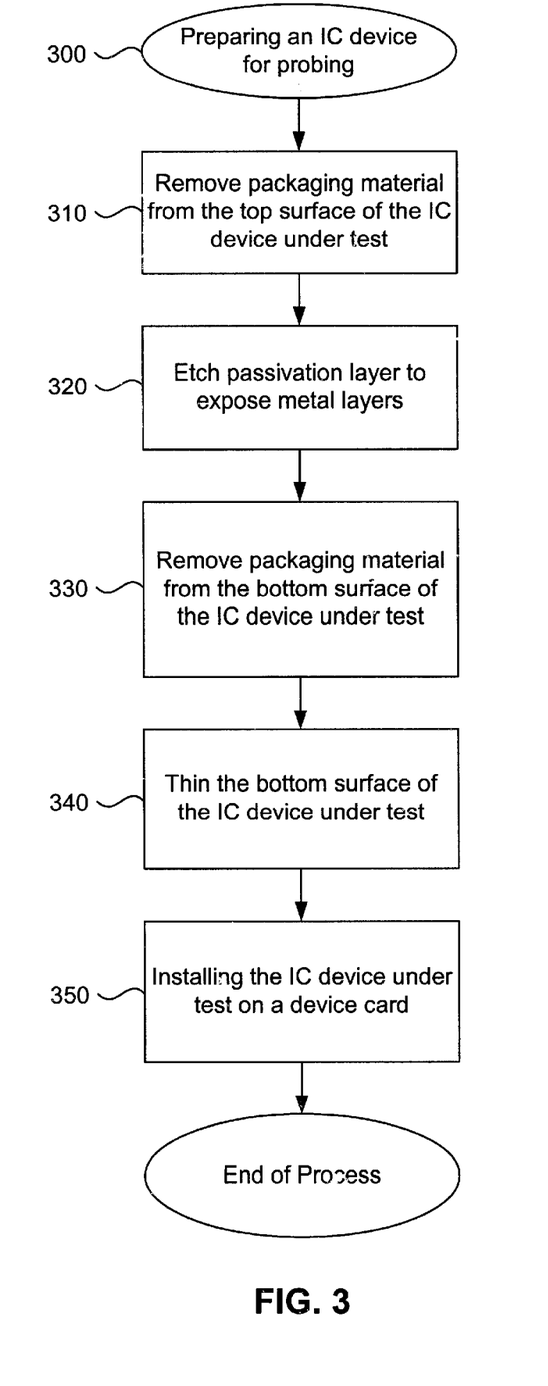
FIG. 3 is flow diagram describing one implementation of the method for preparing an IC device for testing.

FIG. 3 illustrates a method for preparing a packaged IC device 300 for testing according to one implementation of the invention. Since both the front and backside of the IC are to be probed, both of the respective surfaces must be prepared. The method for preparing the IC device begins in block 310 by preparing the front side of the IC for electron beam probing. First, the packaging material is removed from the top surface of the IC. This may be performed using any appropriate technique including decapsulating the plastic packaging material or chemically removing the package material. The packaging material commonly is a plastic or epoxy molding material. Then, in block 320, the passivation layer material is removed so that the underlying metal layer is exposed. This may be performed with chemical etching methods, reactive ion etching or by dry etching. In many cases, IC devices have multiple layers of metal interconnection traces separated by dialectric material. Since electron beams are only capable of probing exposed surfaces, the electron beam may probe the metal interconnections in the top metal layer after the passivation material is removed. In some implementations of the preparation method, it is possible to remove the dialectric material beneath the top metal layer. By removing this additional amount of dialetric material, certain areas of the underlying metal layers are made visible to the electron beam. These visible areas of underlying metal layers may then also be electron beam probed.

In block 330, preparation of the backside begins by removing the packaging material in order to expose the underlying semiconductor material. This may be performed by the same methods as discussed in block 310. In alternative embodiments, packaging material may be removed from both the front and backsides of the IC device in step 310. As will be appreciated by those skilled in the art, some packaging arrangements do not have packaging material on either the front of backsides of a die. In such arrangements, the associated packaging material removal steps can be eliminated. In other packaging arrangements multiple layers of material may be provided and it is contemplated that all such layers would be removed that are necessary to expose the die.

In block 340 the thickness of the layer of semiconductor material is reduced by a removal process, such as chemical etching. The thinned silicon substrate allows the photon beam to more easily penetrate to the doped regions within the semiconductor material. In some implementations, the semiconductor material is reduced to approximately 100 um in thickness. Finally, in block 350, the prepared IC is installed in the DUT card 170, which in turn will be placed within the debug system 100.

Figure 4A:
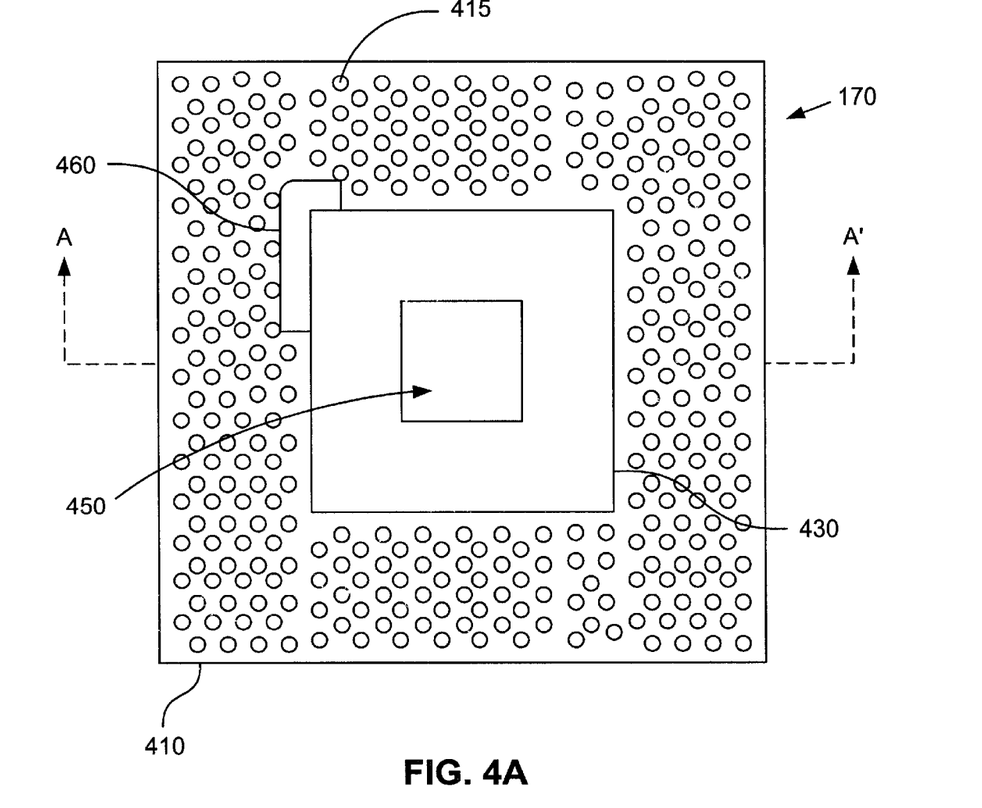
FIG. 4A illustrates the top plan view of one embodiment of the DUT card.
Figure 4B:
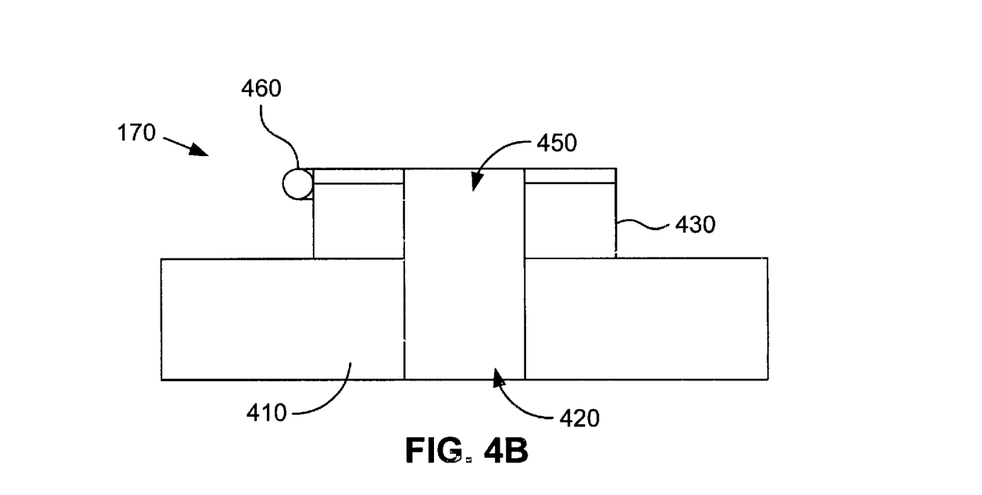
FIG. 4B illustrates the cross-sectional view of the DUT card of FIG. 4A along line A–A'.

FIG. 4A illustrates the top plan view of one embodiment of the DUT card 170. FIG. 4B illustrates the cross-sectional view of the DUT card 170 of FIG. 4A along line A–A'. As shown in FIG. 4A, the DUT card 170 includes a socket 430 which is attached to the top surface of a circuit card 410. The socket 530 includes a socket opening 450 which extends from the top surface to the bottom surface of the socket. The socket opening 450 is sized to receive and hold an IC device which has been prepared for testing. The circuit card 410 includes a circuit card opening 420 which extends from the top surface to the bottom surface of the circuit card. The circuit card opening 420 is aligned with the socket opening 450 so that the backside of the IC is accessible to a beam probe. The front side of the IC is also accessible to a beam probe. The circuit card 410 also includes cable connection points 415 which are connected to interconnection traces which lead to the input and output contacts of the device under test. The cable connection points 415 allow a test system to transmit signals to and from the device under test for failure analysis purposes. As may be appreciated, the socket 430, the circuit card 410, and their respective openings may be tailored to secure variously sized IC's. Also the circuit card 410 should be designed to contain at least as many cable connection points 415 as there are input and output contacts on the IC.

In this embodiment of the socket 430, a locking bar 460 is connected to the socket. The locking bar 460 may be turned between two positions. In one position, the locking bar 460 places a locking mechanism in an open position so that the socket opening 450 may receive the prepared IC. By swinging the locking bar 460 into the second position, the locking bar places the locking mechanism in a closed position such that an inserted IC is locked within the socket opening 450. By locking the IC into socket 430, the chance of damaging the IC while handling the DUT card 170 or during the testing process is reduced. The locking mechanism may be one of a variety of mechanisms capable of securing an IC within the socket. Such mechanisms may be a plastic tab, extended prongs, a sliding frame, etc. Also, the locking bar 460 may be one of a variety of mechanisms capable of manipulating the locking mechanism between a locked and an open position. Such mechanisms may be a twisting knob, a flip-switch, etc. Of course, the locking mechanism could also be manually manipulated between locked and open positions without the use of a special manipulating mechanism.

Figure 5A:
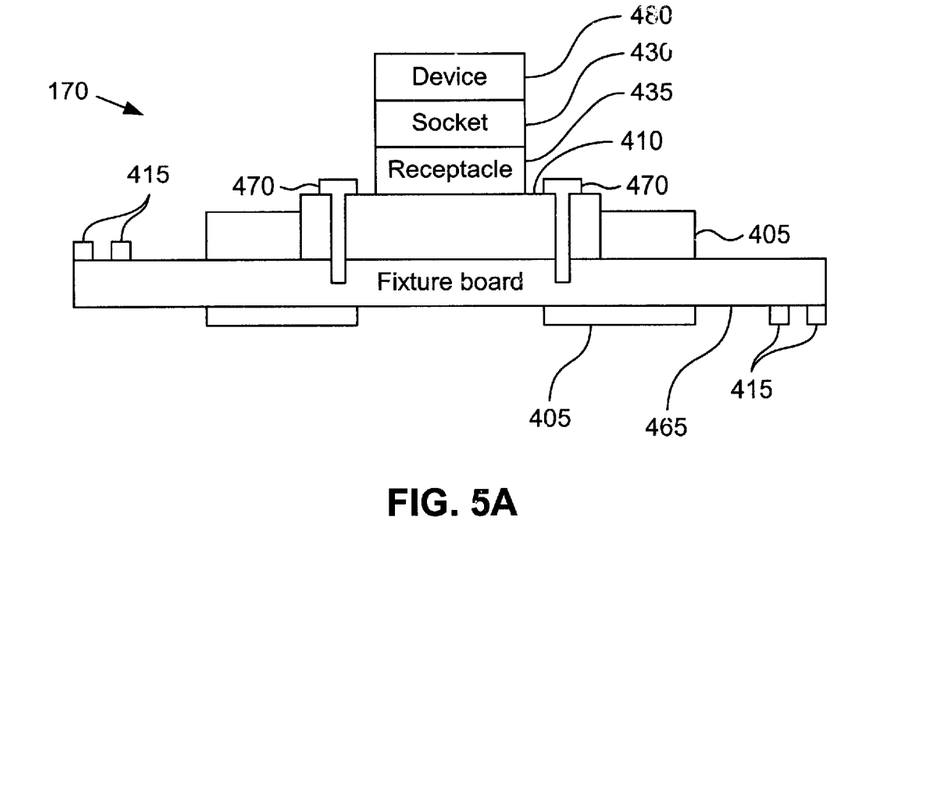
FIG. 5A illustrates a side plan view of an alternative embodiment of the DUT card.
Figure 5B:
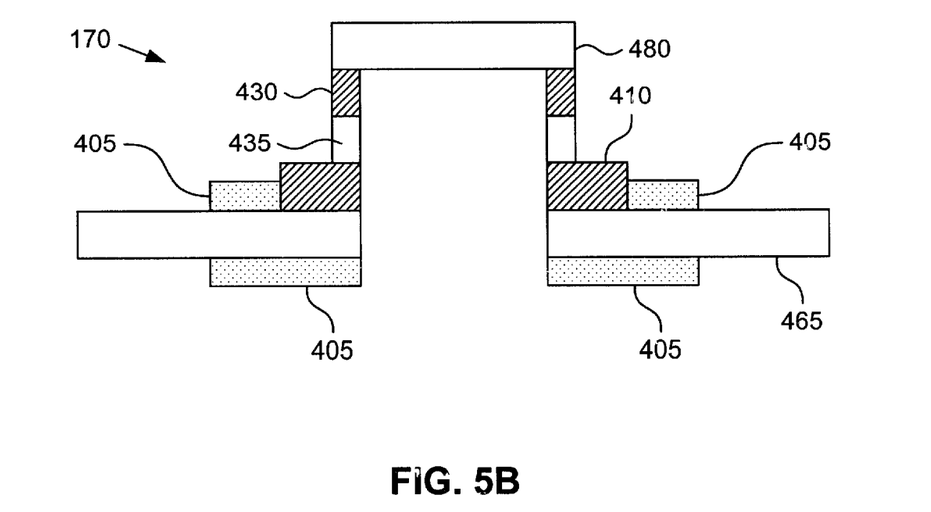
FIG. 5B illustrates a cross-sectional view of the DUT card in FIG. 5A.

FIG. 5A illustrates a side plan view of an alternative embodiment of the DUT card 170. FIG. 5B illustrates a cross-sectional view of the DUT card 170 in FIG. 5A. As shown in FIG. 5A a device under test 480 is attached to the socket 430. A receptacle 435, in turn, is connected to the bottom of the socket 430. The receptacle 435 serves as a common connection structure between the socket 430 and the circuit card 410, which is connected to the opposite side of receptacle 435 from the socket 430. The circuit card 410 is attach to the top of the fixture board 465 by four screws 470. As can be seen in the cross-sectional view of FIG. 5B, the socket 430, receptacle 435, circuit card 410, and the fixture board 465 all have respective openings which are commonly aligned such that the bottom surface of the device under test may be photon beam probed. As may be appreciated, the number of screws used to secure the circuit card 410 and the fixture board 465 may vary according to the dimensions of the DUT card 170 and the characteristics of the debug system 100.

The fixture board 465 is sized large enough such that the edges of the fixture board extend past the outside surfaces of the electron beam probe 110 and the second test chamber 150 after the electron beam probe 110 and the second test chamber 150 are attached to the top and bottom surfaces, respectively, of the DUT card 170. Cables from a testing system can then be easily attached to the cable connection points 415 located on the edges of the fixture board 465. Vacuum seal gaskets 405 are positioned on both sides of the fixture board 465 at points where the electron beam probe 110 and the second test chamber 150 will be attached. The vacuum seal gaskets 405 help maintain the vacuum pressure within the debug system 100.

Figure 6:
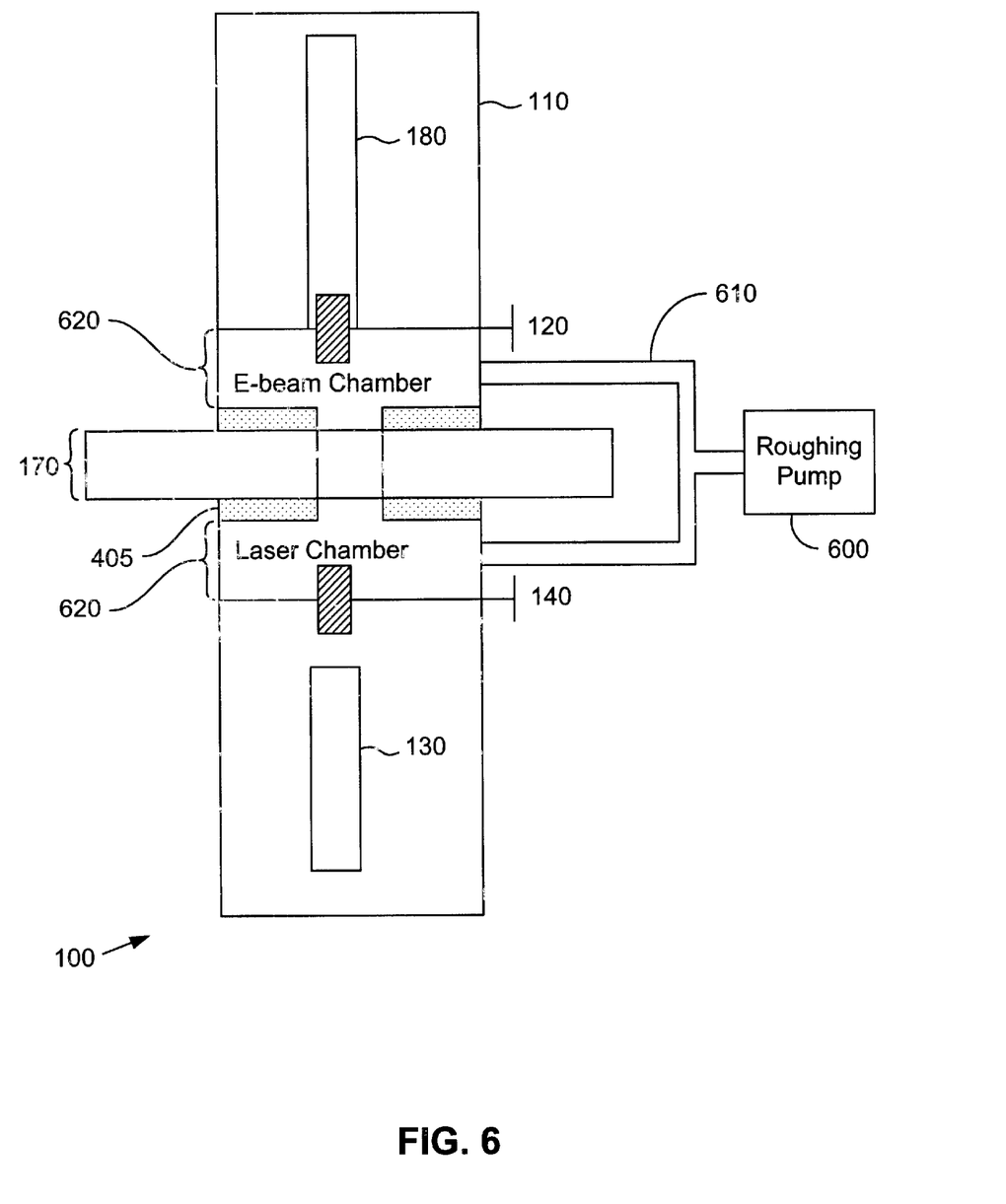
FIG. 6 illustrates an alternative embodiment of the debug system.

FIG. 6 illustrates the debug system 100 according to an alternative embodiment of the present invention. In this embodiment, the interface area 620 is pumped to a vacuum pressure since the electron beam probe 110 must be operated under vacuum pressure. The interface area 620 includes the area in the debug system 100 between the first valve 120 and the second valve 140 which contains the DUT card 170. A "U"-shaped manifold 610 with vacuum seals on both ends is connected to the interface area 620 in a position above and below the DUT card 170. The manifold 610 is then connected to a roughing pump 600. If the electron beam probe 110 is to be used, valve one 120 and valve two 140 are closed. The roughing pump 600 then pumps the electron beam column 180 and the interface area 620 down to a desired vacuum pressure. When the interface area 620 reaches the desired vacuum pressure, valve one 120 is opened so to allow the electron beam probe 110 to focus upon the device under test. The ability to separately pump down the interface area 620 and the electron beam column 180 allows for the debug system 100 to be pumped down faster, as compared to when the two areas are pumped down with only one pump connection at the electron beam column 180. When the photon beam probe 130 is to be used, valve one 120 is closed, roughing pump is turned off, and then valve two 140 is opened.

Figure 7:
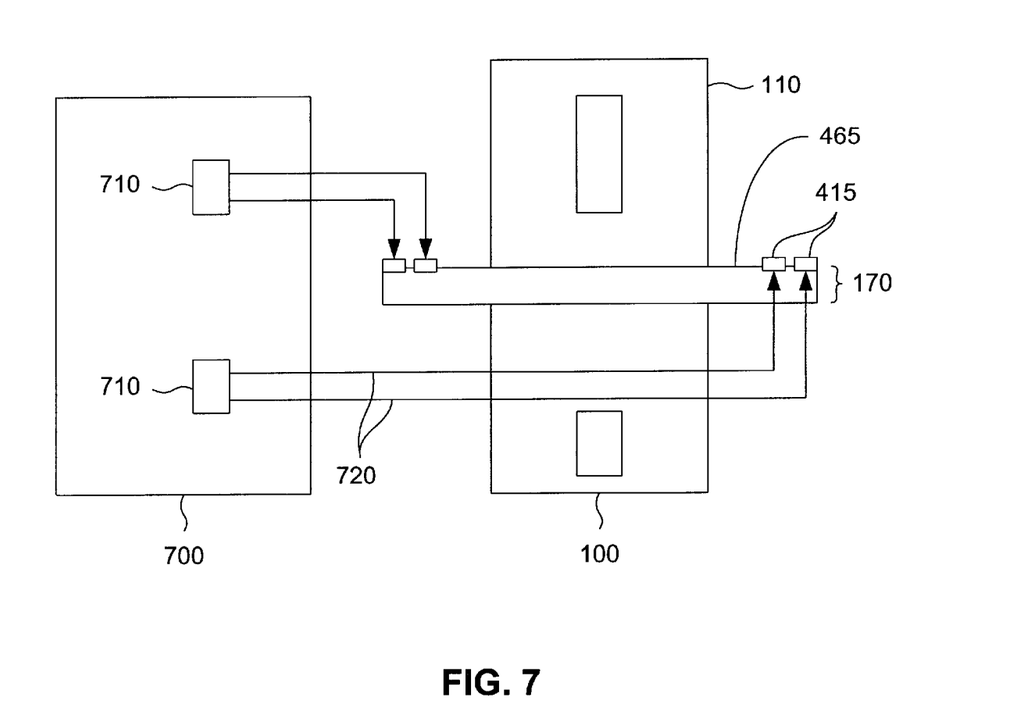
FIG. 7 illustrates the debug system connected to a testing system.

FIG. 7 illustrates the debug system 100 connected to a testing system 700. Stimulation signals are generated by the testing system 700 from testing channels 710 and are sent to the device through the cables 720. When the signals reach the DUT card 170, they are redistributed by the fixture board 465 and forwarded to the device under test. This procedure is called device stimulation during failure analysis. As may be appreciated, the stimulation signals generated by the testing system 700 will vary according to the specific mode of testing being performed.

While this invention has been described in terms of several preferred embodiments, there are alteration, permutations, and equivalents which fall within the scope of this invention. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

We claim:

1. A system for probing an integrated circuit (IC) device under test which has been prepared for probing, the system comprising:
    an electron beam probe configured to direct an electron beam onto a first side of the IC device under test to electron probe the IC device under test;
    a first valve for selectively isolating the electron beam probe from the IC device under test, the first valve being located proximate to the first side of the IC device;
    a photon beam probe configured to direct a photon beam onto a second side of the IC device under test to photon probe the IC device under test, the photon probe being positioned on an opposite side of the IC device under test from the electron beam probe; and
    a second valve for selectively isolating the photon probe from the IC device under test, the second valve being positioned on an opposite side of the IC device under test from the first valve and also being positioned proximate to the opposite side of the IC device.

2. The system for probing as recited in claim 1 further comprising:
    a first test chamber which includes the area in between the first side of the IC device under test and the first valve; and
    a second test chamber which includes the area in between the second side of the IC device under test and the second valve, wherein the second valve is arranged to facilitate the maintenance of a vacuum within at least the first test chamber and the second test chamber during electron beam probing.

3. The system for probing as recited in claim 2 further comprising a device card holder disposed between the first and second valves, the device card configured to secure the IC device under test and to provide a vacuum seal between the first and second test chambers.

4. The system for probing as recited in claim 1 further comprising an electron beam column within which the electron beam travels, the electron beam column being located within the electron beam probe, the first valve being arranged to selectively isolate the IC device under test from the electron beam column to facilitate maintaining a vacuum within the electron beam column.

5. The system for probing as recited in claim 1 further comprising a device card holder disposed between the first and second valves, the device card configured to secure the IC device under test.

6. A method for probing an integrated circuit (IC) device under test using a test system that includes an electron beam probe on a first surface of the IC device under test and a photon beam probe on a second surface of the IC device under test, the method comprising the sequential operations of:
    inserting a device card that carries the IC device under test into the test system;
    isolating the IC device under test from the photon probe;
    exposing a vacuum chamber within the electron beam probe to the IC device under test and applying a vacuum to a region around the IC device under test to facilitate electron beam probing of the IC device under test;
    electron beam probing the first surface of the IC device under test;
    isolating the IC device under test from the electron beam probe to help maintain a vacuum in the vacuum chamber within the electron beam probe;
    exposing the photon beam probe to the second surface of the IC device under test; and
    photon beam probing the second surface of the IC device under test.

7. The method for probing an IC device under test as recited in claim 6 further comprising recording data resulting from electron probing the first surface of the IC device under test.

8. The method for probing an IC device under test as recited in claim 6 further comprising recording data resulting from photon probing the second surface of the IC device under test.

9. The method for probing an IC device under test as recited in claim 6 further comprising positioning a photon beam probe lens to a position proximate to the second surface of the IC device under test.

10. The method for probing an IC device under test as recited in claim 9 further comprising moving the photon beam probe lens away from the second surface of the IC device under test.

11. The method for probing an IC device under test as recited in claim 6 further comprising removing the device card out from the test system.

* * * * *